United States Patent [19]
Forestier et al.

[11] Patent Number: 5,175,340
[45] Date of Patent: Dec. 29, 1992

[54] NEW LIPOSOLUBLE UNSATURATED BENZALMALONATE DERIVATIVES AND THEIR USE AS ABSORBERS FOR ULTRAVIOLET RADIATION IN COSMETICS

[75] Inventors: Serge Forestier, Claye-Souilly; Gerard Lang, Saint-Gratien; Herve Richard, Paris, all of France

[73] Assignee: L'Oreal, Paris, France

[21] Appl. No.: 375,820

[22] Filed: Jul. 5, 1989

[30] Foreign Application Priority Data

Jul. 8, 1988 [LU] Luxembourg .......................... 87271

[51] Int. Cl.$^5$ .............................................. C07C 69/76
[52] U.S. Cl. ...................................... 560/55; 556/437; 514/844; 514/880; 424/60
[58] Field of Search .................... 560/55; 556/437; 424/60; 514/844, 880

[56] References Cited

FOREIGN PATENT DOCUMENTS

| | | |
|---|---|---|
| 0100651 | 2/1984 | European Pat. Off. |
| 146730 | 7/1985 | European Pat. Off. |
| 3424066 | 1/1986 | Fed. Rep. of Germany |
| 2019952 | 7/1970 | France |
| 2515662 | 11/1982 | France |
| 1037169 | 7/1966 | United Kingdom |

OTHER PUBLICATIONS

*Journal of the Chemical Society*, Perkin Transactions 1, No. 8, 1985, pp. 1627–1635, Chemical Society, Letchwork, GB; S. P. Breukelman et al.: "Preparation and Some Reactions of 4- and 5-aryl-4, 5-dihydropyridazin-3(2H)-ones".

*Primary Examiner*—Paul J. Killos
*Attorney, Agent, or Firm*—Marshall, O'Toole, Gerstein, Murray & Bicknell

[57] ABSTRACT

The invention relates to an unsaturated benzalmalonate derivative of formula:

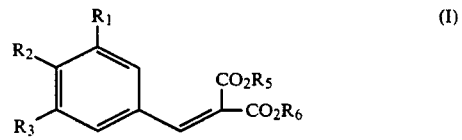

in which:

$R_1$ and $R_2$ denote a hydrogen atom, a hydroxyl, a trimethylsiloxy, a $C_1$-$C_6$ straight or branched chain alkyl, $C_1$-$C_6$ straight or branched chain alkoxy or a $-(CH_2)_p-C(R_4)=CH_2$ radical, where p is an integer between 1 and 10 and preferably between 1 and 4 and $R_4$ denotes a hydrogen atom or a $C_1$-$C_4$ straight or branched chain alkyl radical, one of the two radicals $R_1$ or $R_2$ denoting a residue $-(CH_2)_p-C(R_4)=CH_2$, $R_3$ denotes a hydrogen atom, a $C_1$-$C_6$ straight or branched chain alkyl radical or a $C_1$-$C_6$ straight or branched chain alkoxy radical, $R_5$ and $R_6$, which are identical or different, denote a $C_1$-$C_8$ straight or branched chain alkyl radical.

Use as a sunscreen in cosmetic compositions.

14 Claims, No Drawings

NEW LIPOSOLUBLE UNSATURATED BENZALMALONATE DERIVATIVES AND THEIR USE AS ABSORBERS FOR ULTRAVIOLET RADIATION IN COSMETICS

The present invention relates to new liposoluble unsaturated benzalmalonate derivatives and to their use in the field of cosmetics as absorbers of ultraviolet radiation for protecting human skin and hair against solar radiation, as well as for stabilizing cosmetic compositions containing photosensitive constituents.

It is known that light radiations of wavelengths between 280 nm and 400 nm allow human skin to tan and that rays of wavelengths of between 280 and 320 nm, known by the name of UV-B, cause erythemas and skin burns which can be harmful to the development of the suntan; this UV-B radiation must therefore be filtered out.

It is also known that UV-A rays, of wavelengths between 320 and 400 nm, causing skin to tan, are capable of inducing a deterioration in the latter, especially in the case of a sensitive skin or of a skin which is continuously exposed to solar radiation. In particular, UV-A rays produce a loss of skin elasticity and the appearance of wrinkles, leading to premature aging. They promote the triggering of an erythematous reaction or intensify this reaction in certain individuals and may even be at the source of phototoxic or photoallergic reactions.

It is therefore advantageous to have available compounds absorbing UV rays over a broad band, in order to be able to filter out both UV-A and UV-B rays.

It is known, furthermore, that the constituents forming part of cosmetic preparations do not always have a sufficient stability to light and that they are degraded by the action of light radiations.

Consequently, it is desirable to incorporate in these preparations compounds capable of filtering out UV rays, which must, in addition, exhibit good stability and sufficient solubility in the media usually employed in cosmetics, and in particular in oils and fats.

It is also desirable to provide hair with good protection against photochemical degradation in order to avoid, in particular, bleaching or a change in shade.

Thus, the Applicant Company surprisingly found, in the course of its research, that certain unsaturated liposoluble benzalmalonate derivatives had good filtering properties in a broad range of wavelengths stretching from 280 to 360 nm. In addition to their good filtering properties, the new liposoluble benzalmalonate derivatives have an excellent chemical and photochemical stability and have the advantage of being neither toxic nor irritant and of being perfectly innocuous towards the skin.

They also have an excellent liposoluble nature, which makes them usable in the fatty substrates employed in cosmetics and in particular in compositions intended to protect human skin against UV rays, and more particularly in sunscreen compositions.

The subject of the present invention is therefore the new liposoluble unsaturated benzalmalonate derivatives of formula:

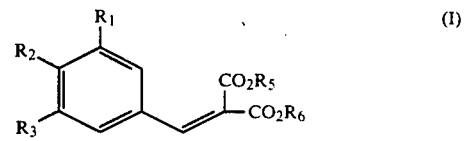

in which:
$R_1$ and $R_2$ denote a hydrogen atom, a hydroxyl radical, a trimethylsiloxy radical, a $C_1$-$C_6$ straight or branched chain alkyl radical, a $C_1$-$C_6$ straight or branched chain alkoxy radical or a radical —$(CH_2)_p$—$C(R_4)$=$CH_2$, in which p denotes an integer between 1 and 10 and preferably between 1 and 4 and $R_4$ denotes a hydrogen atom or a $C_1$-$C_4$ straight or branched chain alkyl radical, one of the two radicals $R_1$ or $R_2$ denoting a residue —$(CH_2)_p$—$C(R_4)$=$CH_2$,
$R_3$ denotes a hydrogen atom, a $C_1$-$C_6$ straight or branched chain alkyl radical or a $C_1$-$C_6$ straight or branched chain alkoxy radical,
$R_5$ and $R_6$, which are identical or different, denote a $C_1$-$C_8$ straight or branched chain alkyl radical.

Among the $C_1$-$C_6$ straight or branched chain alkoxy radicals there may be mentioned, for example, methoxy, ethoxy, n-propoxy, isopropoxy, n-butoxy, isobutoxy, tertbutoxy, n-amyloxy, isoamyloxy, neopentyloxy and n-hexyloxy radicals.

Among the $C_1$-$C_6$ straight or branched chain alkyl radicals there may be mentioned more particularly methyl, ethyl, n-propyl, isopropyl, n-butyl, isobutyl, tertbutyl, n-amyl, isoamyl, neopentyl and n-hexyl radicals, and among $C_1$-$C_8$ alkyl radicals, the preceding radicals as well as n-heptyl, n-octyl and 2-ethylhexyl radicals.

The following compounds may be mentioned among the preferred compounds of the invention of formula (I):
diethyl 3-allyl-4-hydroxybenzalmalonate,
diethyl 3-allyl-4-methoxybenzalmalonate,
diethyl 3-methallyl-4-methoxybenzalmalonate,
diethyl 4-allylbenzalmalonate,
diethyl 4-methallylbenzalmalonate,
diethyl 3-allyl-4,5-dimethoxybenzalmalonate,
diethyl 3-allyl-4-butoxy-5-methoxybenzalmalonate,
di-(2-ethylhexyl) 3-allyl-4,5-dimethoxybenzalmalonate.

The compounds of formula (I) according to the invention are prepared by a Knoevenagel reaction, namely condensation of an aromatic aldehyde (II) with a malonic acid diester of formula (III) in toluene in the presence of piperidinium acetate as catalyst. The water is removed azeotropically. The reaction scheme is the following:

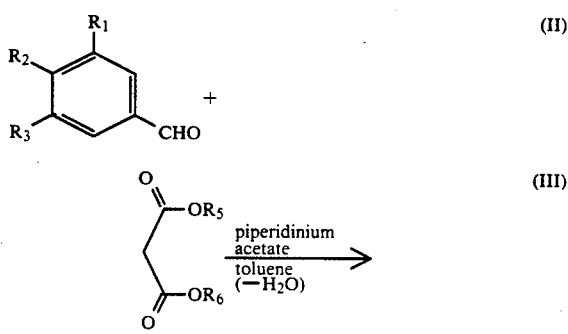

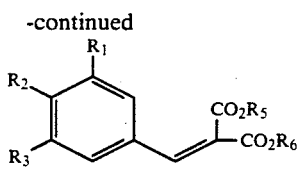

$R_1$, $R_2$, $R_3$, $R_5$ and $R_6$ having the meanings shown above for formula (I).

The products are recrystallized, distilled or separated by column chromatography. The aldehydes of formula (II), which are known compounds, may be obtained according to one of the following methods:

FIRST METHOD

The aldehyde of formula (II) in which $R_1$ denotes a residue $-(CH_2)_p-C(R_4)=CH_2$ when $p=1$, $R_2$ denotes a hydroxyl residue and $R_3$ has the abovementioned meaning, which has the formula (IIA), may be obtained by a Claisen rearrangement of an aldehyde of formula (IV) according to the following reaction scheme:

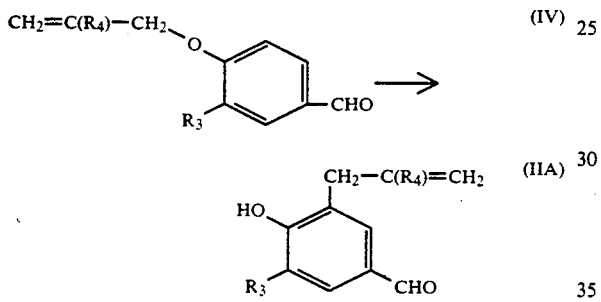

This rearrangement can be carried out under the conditions described by Tarbell (Organic Reactions, vol. 2, John Wiley, New York, 1944, page 1) by heating the compound of formula (IV) to at least approximately 170° C., optionally in the presence of a solvent.

The aldehyde of formula (IV) may be obtained by reaction of an alkenyl halide of formula (V) with an aldehyde of formula (VI):

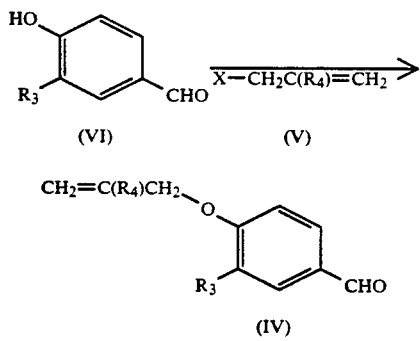

This reaction is carried out in the presence of a base in a solvent, for example in the presence of an alkali metal carbonate in dimethylformamide, at a temperature between the ambient temperature and the boiling point of the solvent. The aldehyde of formula (VI) can be prepared by known methods. In the compound of formula (V), X denotes a halogen atom, preferably a chlorine or bromine atom.

SECOND METHOD

The aldehyde of formula (IIB) corresponding to formula II in which R denotes a residue $-(CH_2)_p-C(R_4)=CH_2$ when $p=1$, $R_2$ denotes a $C_1-C_6$ alkoxy residue and $R_3$ has the abovementioned meaning can be obtained according to either of the two routes below:

FIRST ROUTE

By formylation of a phenol ether of formula (VII) according to the following reaction scheme:

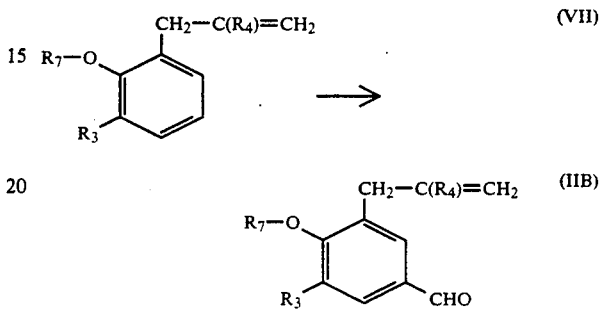

$R_7$ denotes a $C_1-C_6$ alkyl radical, $R_3$ having the abovementioned meaning.

This reaction is carried out, for example, by virtue of the addition of the complexes formed by the action of phosphorus oxychloride on disubstituted formamides according to Vilsmeier and Haack (Ber., 60, p.119, 1927) to the compounds of formula (VII).

The phenol ether (VII) can be prepared by known methods.

SECOND ROUTE

The compound of formula (IIA) obtained by the first method can be converted into a compound of formula (IIB) by reaction with a $C_1-C_6$ alkyl halide or sulphate in the presence of a base, for example in the presence of an alkali metal carbonate in a solvent such as dimethylformamide, or else in the presence of an alkali metal hydride in 1,2-dimethoxyethane, according to the following reaction scheme:

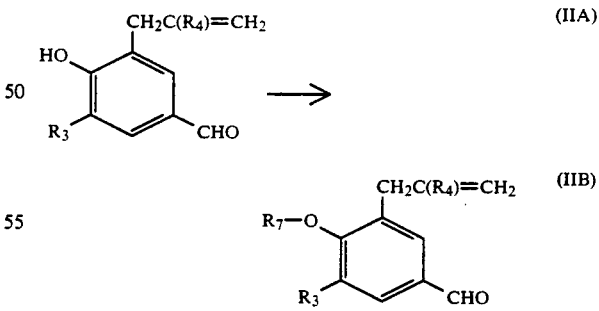

THIRD METHOD

The aldehyde of formula (II) in which $R_1$ or $R_2$ denotes a residue $-(CH_2)_p-C(R_4)=CH_2$ and $R_3$ denotes a hydrogen atom, a $C_1-C_6$ alkyl residue or a $C_1-C_6$ alkoxy residue can also be obtained by reaction of ethyl orthoformate with a phenylmagnesium bromide of formula (VIII), followed by a hydrolysis of the acetal formed:

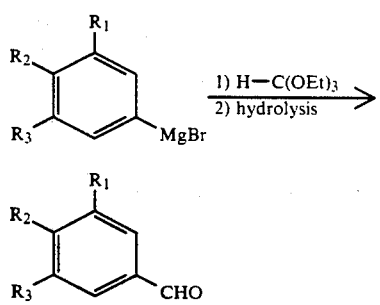

$$\text{(VIII)} \xrightarrow[\text{2) hydrolysis}]{\text{1) H—C(OEt)}_3} \text{(II)}$$

This reaction can be carried out under the conditions described by Quelet (C. R. Acad. Sci. vol. 182, p.1285 and Bull. Soc. Chim. Fr. vol. 45, p.267), for example in an inert solvent such as ethyl ether, dioxane or 1,2-dimethoxyethane, at a temperature between the ambient temperature and the boiling point of the solvent. In the compounds of formula (II) and (VIII) one of the substituents $R_1$ or $R_2$ denotes a radical —$(CH_2)_p$—$C(R_4)=CH_2$, $R_4$ and p having the abovementioned meanings, and the other denotes a hydrogen atom, a $C_1$-$C_6$ alkyl radical or a $C_1$-$C_6$ alkoxy radical and $R_3$ denotes a hydrogen atom, a $C_1$-$C_6$ alkyl radical or a $C_1$-$C_6$ alkoxy radical.

Owing to their liposoluble nature, the unsaturated benzalmalonate derivatives of formula (I) above become evenly distributed in conventional cosmetic substrates containing at least one fatty phase, and can be applied to skin or to hair to form an effective protective film.

Another subject of the present invention is therefore a cosmetic composition comprising, in a cosmetically acceptable substrate containing at least one fatty phase, an effective quantity of at least one unsaturated benzalmalonate derivative of formula (I) above.

The cosmetic composition of the invention may be employed as a composition for protecting human skin or hair or as a sunscreen composition.

Another subject of the present invention is a process for protecting skin and natural or sensitized hair against solar radiation, consisting in applying to the skin or hair an effective quantity of at least one compound of formula (I), contained in a cosmetically acceptable substrate containing at least one fatty phase.

"Sensitized hair" means hair which has undergone a permanent-waving, dyeing or bleaching treatment.

A further subject of the invention is a coloured or uncoloured cosmetic composition stabilized to light, comprising an effective quantity of at least one benzalmalonate derivative of formula (I) above.

When employed as a composition intended to protect human skin against ultraviolet rays, the cosmetic composition according to the invention may be in the most diverse forms usually employed for a composition of this type. It may be especially in the form of oily or oleo-alcoholic lotions, of emulsions such as a cream or a milk, of oleoalcoholic, alcoholic or hydroalcoholic gels, of solid sticks, or it may be packaged as an aerosol.

It may contain the cosmetic adjuvants usually employed in a composition of this type, such as thickeners, softeners, humectants, surfactants, preserving agents, antifoams, perfumes, oils, waxes, lanolin, propellants, colorants and/or pigments for the purpose of colouring the composition itself or the skin, or any other ingredient usually employed in cosmetics.

The compound of formula (I) is present in proportions by weight of between 0.25 and 3% relative to the total weight of the cosmetic composition for protecting human skin.

The solubilizing solvent used may be an oil, a wax and, in general, any fatty substance, a lower monoalcohol or polyol or mixtures thereof. The monoalcohols or polyols which are more particularly preferred are ethanol, isopropanol, propylene glycol, glycerine and sorbitol.

One embodiment of the invention is an emulsion in the form of a protective cream or milk comprising, in addition to the compound of formula (I), fatty alcohols, fatty acid esters and especially fatty acid triglycerides, fatty acids, lanolin, natural or synthetic oils or waxes and emulsifiers, in the presence of water.

Another embodiment consists of oily lotions based on natural or synthetic oils and waxes, lanolin, and fatty acid esters, especially fatty acid triglycerides, or of oleoalcoholic lotions based on a lower alcohol such as ethanol or a glycol such as propylene glycol and/or a polyol such as glycerine and oils, waxes and fatty acid esters such as fatty acid triglycerides.

The cosmetic composition of the invention may also be an alcoholic gel comprising one or more lower alcohols or polyols such as ethanol, propylene glycol or glycerine and a thickener such as silica. Oleoalcoholic gels additionally contain a natural or synthetic oil or wax.

The solid sticks consist of natural or synthetic waxes and oils, fatty alcohols, fatty acid esters, lanolin and other fatty substances.

In the case of a composition packaged as an aerosol, traditional propellants such as alkanes, fluoroalkanes and chlorofluoroalkanes are employed.

The present invention is also aimed at cosmetic sunscreen compositions containing at least one compound of formula (I) and capable of containing other UV-B and/or UV-A filters.

In this case, the total quantity of filters present in the sunscreen composition, that is to say the compound of formula (I) and optionally the other filters, is between 0.5 and 15% by weight relative to the total weight of the sunscreen composition.

These sunscreen compositions are in the forms indicated above for compositions for protecting human skin.

When the cosmetic composition according to the invention is intended to protect natural or sensitized hair against UV rays, this composition may be in the form of a shampoo, lotion, gel or emulsion for rinsing or application before or after shampooing, before or after dyeing or bleaching, before or after permanent-waving, a styling or treating lotion or gel, a lotion or gel for blow drying or setting, a hair lacquer, or a composition for permanent-waving, dyeing or bleaching hair. In addition to the compound of the invention, this composition may contain various adjuvants employed in a composition of this type, such as surfactants, thickeners, polymers, softeners, preserving agents, foam stabilizers, electrolytes, organic solvents, silicone derivatives, oils, waxes, antigrease agents, colorants and/or pigments intended to colour the composition itself or the hair, or any other ingredient usually employed in the field of hair care.

It contains 0.25 to 3% by weight of compound of formula (I).

The present invention is also aimed at cosmetic compositions containing at least one compound of formula (I) as an agent for protection against ultraviolet rays, consisting of hair-care compositions such as hair lacquers, optionally treating or disentangling setting lotions, dyeing shampoos, hair-tinting compositions; of makeup products such as nail varnishes, treatment creams and oils for the skin, makeup foundations, lipsticks, compositions for skin care such as bath oils or creams, as well as any other cosmetic composition capable of presenting problems of stability to light during storage as a result of its constituents.

Such compositions contain 0.25 to 3% by weight of compound of formula (I).

The invention is also aimed at a process for protecting cosmetic compositions against ultraviolet rays, consisting in incorporating in these compositions an effective quantity of at least one compound of formula (I).

The invention will be illustrated better, without, however, being limited, by the following illustrative embodiments.

EXAMPLES OF PREPARATION

EXAMPLE 1

Diethyl 3-allyl-4-methoxybenzalmalonate

Preparation of a compound of general formula (I) in which $R_1$ denotes the radical $-CH_2-CH=CH_2$, $R_2$ denotes the radical $-OCH_3$, $R_3$ denotes a hydrogen atom and $R_5$ and $R_6$ denotes the radical $-C_2H_5$:

FIRST STAGE

Preparation of 3-allyl-4-methoxybenzaldehyde

First method:

50 g (0.308 moles) of 4-allyloxybenzaldehyde are heated to 220° C. for 4 hours under nitrogen and with stirring. The cooled reaction mixture is taken up in dichloromethane and is extracted with 5N sodium hydroxide. The aqueous phase is acidified with 6N hydrochloric acid and extracted with dichloromethane. The organic phase is dried and the solvent evaporated off, to give a brown-black oil. After vacuum distillation the fraction, of bp=138°-140° C. at 106 Pa is collected (15 g, yield=30%) as 3-allyl-4-hydroxybenzaldehyde (white powder, mp=66° C.).

The above derivative (14.5 g, 0.089 moles), 30 ml of N,N-dimethylformamide, 13.6 g (0.098 moles) of anhydrous potassium carbonate and 11 ml (0.178 moles) of methyl iodide are introduced in succession. The whole is heated to 60°-70° C. for 3 hours. The reaction mixture is poured into iced water and the whole is extracted with diisopropyl ether. The organic phase is dried over sodium sulphate, is filtered, and the solvent is evaporated off to obtain 3-allyl-4-methoxybenzaldehyde (pale yellow oil, 13.6 g, yield =87%).

Second method:

2-Allylphenol (100 g, 0.75 mole), 2 liters of dry N,N-dimethylformamide and anhydrous potassium carbonate (206 g, 1.49 moles) are introduced in succession into a 5-liter reactor. Methyl iodide (92 ml, 1.49 moles) is introduced dropwise at ambient temperature. The mixture is left at 38° C. for 4 hours. The reaction mixture is poured into iced water and is extracted with dichloromethane. The organic phase is washed with water and dried. After evaporation of the solvent and vacuum distillation, a fraction of 2-allylanisole distilling at 110° C. at 5,000 Pa is recovered (colourless liquid, 46 g, yield=42%).

N,N-Dimethylformamide (75 ml, 0.98 moles) is placed in a 500-ml reactor, and phosphorus oxychloride (26 ml, 0.28 moles) is added, while cooling to about 5° C. The mixture is kept at 10° C. for one hour and the preceding derivative (41.5 g, 0.28 moles) is introduced dropwise. The temperature is raised gradually to 100° C. over one hour and the reaction mixture is kept at this temperature for 10 hours. The cooled mixture is poured into iced water and is extracted with diisopropyl ether. The organic phases are washed with water, are dried over sodium sulphate, are filtered, and the solvent is evaporated off to give a crude product (31 g), which is purified by chromatography on silica 60 (eluent: 50:50 toluene/hexane) to give a fraction (4.5 g) of 3-allyl-4-methoxybenzaldehyde identical with that obtained by the first method.

SECOND STAGE

Preparation of diethyl 3-allyl-4-methoxybenzalmalonate

A mixture of the preceding derivative (10 g, 0.057 moles), diethyl malonate (9.09 g, 0.057 moles), toluene (15 ml), acetic acid (0.36 ml) and piperidine (0.68 ml) is heated under reflux, under nitrogen, using a Dean Stark. After 5 hours, heating, 1 ml of water has been collected. After cooling, the toluene phase is washed with water, is dried and the solvent is distilled off. An orange-coloured oil is obtained, which crystallizes. It is recrystallized from diisopropyl ether with treatment using animal charcoal. White crystals of diethyl 3-allyl-4-methoxybenzalmalonate are obtained (12.7 g, yield =70%), which have the following characteristics:

Melting point: 69° C.

$^1$H NMR spectrum (CDCl$_3$): spectrum consistent with the expected structure.

UV spectrum (CHCl$_3$): $\lambda_{max}$=318 nm,=24450.

Elemental analysis:

Calculated: C,67.91; H,6.97; O, 25.13.

Found: C,68.04; H, 6.89; O, 25.23.

EXAMPLE 2

Diethyl 3-allyl-4,5-dimethoxybenzalmalonate

Preparation of a compound of general formula (I) in which $R_1$ denotes the radical $-CH_2-CH=CH_2$, $R_2$ and $R_3$ denote the radical $-OCH_3$ and $R_5$ and $R_6$ denote the radical $-C_2H_5$ First stage:

4-Allyloxy-3-methoxybenzaldehyde (62.5 g, 0.325 moles) is heated to 180° C. for 6 hours 30 minutes with stirring. Cooling is applied. The brown solid is taken up in dichloromethane and extracted with 5% strength sodium hydroxide. The aqueous phase is acidified with 3N hydrochloric acid. The solid obtained is filtered off and recrystallized from a 40:60 ethanol/water mixture. 3-Allyl-4-hydroxy-5-methoxybenzaldehyde is obtained (light-beige powder, 62.5 g, yield =71%, melting point=83°-84° C.).

Second stage:

The preceding derivative (34 g, 0.18 moles), dimethylformamide (500 ml), potassium carbonate (49 g, 0.35 moles) and methyl iodide (50 g, 0.35 moles) are introduced successively into a reactor. This is kept at a temperature of 40° C. for 3 hours. The reaction mixture is dropped into iced water and the oil formed is extracted with dichloromethane. After washing, drying and evaporating off the solvent, a light-brown oil is obtained, which is passed through a bed of silica 60 to give a pale-yellow oil of 3-allyl-4,5-dimethoxybenzaldehyde (34.3 g, yield =92%).

Third stage:

A mixture of the preceding derivative (15 g, 0.073 moles), diethyl malonate (11.7 g, 0.073 moles), toluene (18 ml), acetic acid (0.46 ml) and piperidine (0.87 ml) is heated for 7 hours under reflux using a Dean Stark. After cooling, the toluene phase is washed with water, is dried and the solvent is distilled off. The pale-orange oil obtained (24.5 g, yield=96%) is crystallized from a 50:50 diisopropyl ether/hexane mixture to give white crystals of diethyl 3-allyl-4,5-dimethoxybenzalmalonate (14.2 g, yield 56%) which has the following characteristics:

Melting point: 43°-44° C.

$^1$H NMR spectrum (CDCl$_3$): spectrum consistent with the expected formula.

UV spectrum (CHCl$_3$): $\lambda_{max}$=303 nm; ,=15700, $\lambda_{max}$=325 nm, $\epsilon$=12830 (shoulder).

Elemental analysis:
Calculated: C, 65.50; H, 6.94; O, 27.55.
Found: C, 65.33; H, 6.91; O, 27.78.

EXAMPLE 3

Di-(2-ethylhexyl) 3-allyl-4,5-dimethoxybenzalmalonate

Preparation of a compound of general formula (I) in which R$_1$ denotes the radical —CH$_2$—CH=CH$_2$, R$_2$ and R$_3$ denote the radical —OCH$_3$ and R$_5$ and R$_6$ denote the radical —CH$_2$CH(C$_2$H$_5$)C$_4$H$_9$.

A mixture of 3 TM allyl-4,5-dimethoxybenzaldehyde (10.3 g, 0.05 moles), di-(2-ethylhexyl) malonate (16.4 g, 0.05 moles), toluene (20 ml), acetic acid (0.41 ml) and piperidine (0.77 ml) is heated to reflux using a Dean Stark. After cooling, washing the toluene phase with water, drying and evaporation of the solvent, an orange-coloured oil is obtained, which is purified by chromatography on a column of silica 60 (eluent: 90:10 heptane/ethyl acetate) to give di-(2-ethylhexyl) 3-allyl-4,5-dimethoxybenzalmalonate (colourless oil, 15 g, yield=64%), which has the following characteristics:

$^1$H NMR spectrum (CDCl$_3$): spectrum consistent with the expected formula.

UV spectrum (CHCl$_3$): $\lambda_{max}$303 nm, $\epsilon$=15550, $\lambda_{max}$=320 nm, $\epsilon$=13430 (shoulder).

Elemental analysis:
Calculated: C, 72.06; H,>9.36; O, 18.58.
Found: C, 72.09; H, 9.44; O, 18.69.

EXAMPLE 4

Diethyl 3-allyl-4-butoxy-5-methoxybenzalmalonate

Preparation of a compound of general formula (I) in which R$_1$ denotes the radical —CH$_2$CH=CH$_2$, R$_2$ denotes the radical —OC$_4$H$_9$, R$_3$ denotes the radical —OCH$_3$ and R$_5$ and R$_6$ denote the radical —C$_2$H$_5$.

First stage:

A mixture of 3-allyl-4-hydroxy-5-methoxybenzaldehyde (10.25 g, 0.053 moles), dimethylformamide (150 ml), potassium carbonate (8.29 g, 0.06 moles) and 1-bromobutane (8.22 g, 0.06 moles) is kept at 40°-45° C. for 3 hours. The reaction mixture is dropped into iced water and the oil formed is extracted with dichloromethane. After washing with water, drying and evaporation of the solvent, a brown oil is obtained, which is passed through a bed of silica 60 to give a pale yellow oil of 3-allyl-4-butoxy-5-methoxybenzaldehyde (13 g, yield=91%).

Second stage:

A mixture of the preceding derivative (10.2 g, 0.041 moles), diethyl malonate (7 g, 0.041 moles), toluene (12 ml), acetic acid (0.26 ml) and piperidine (0.49 ml) is heated under reflux for 7 hours using a Dean Stark. In the same manner as in Example 3, diethyl 3-allyl-4-butoxy-5-methoxybenzalmalonate is obtained (colourless oil, 10 g, yield 67%), which has the following characteristics:

$^1$H NMR spectrum (CDCl$_3$): spectrum consistent with the expected structure.

UV spectrum (CH$_2$Cl$_2$): $\lambda_{max}$=305 nm, $\epsilon$=15500, $\lambda_{max}$=325 nm, $\epsilon$=13530 (shoulder).

Elemental analysis:
Calculated: C, 67.67; H, 7.74; O, 24.58.
Found: C, 67.87; H, 7.83; O, 24.44.

EXAMPLES OF APPLICATION

| Example A - Sunscreen oil The following products are mixed, optionally with heating to 40-45° C. to homogenize: | |
|---|---|
| Cocoa butter | 2.5 g |
| Compound of Example 2 | 1.5 g |
| Butylhydroxyanisole | 0.05 g |
| Perfume q.s. | |
| Vegetable oil q.s. | 100 g |
| Example B - Sunscreen oil | |
| Lanolin | 2.5 g |
| Compound of Example 1 | 3 g |
| Butylhydroxyanisole | 0.05 g |
| Perfume q.s. | |
| C$_8$-C$_{12}$ acid triglycerides q.s. | 100 g |
| Example C - Oleoalcoholic sunscreen lotion | |
| Lanolin | 2.5 g |
| C$_8$-C$_{12}$ fatty acid triglycerides | 40 g |
| Perfume q.s. | |
| Compound of Example 1 | 2 g |
| Butylhydroxytoluene | 0.05 g |
| 96° alcohol q.s. | 100 g |

We claim:

1. Unsaturated benzalmalonate compound of formula:

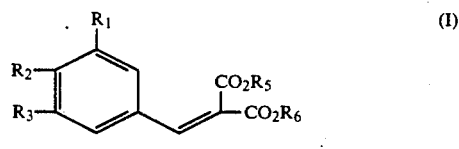

in which:

R$_1$ and R$_2$ denote a hydrogen atom, a hydroxyl radical, a trimethylsiloxy radical, a C$_1$-C$_6$ straight or branched chain alkyl radical, a C$_1$-C$_8$ straight or branched chain alkoxy radical or a radical—(CH$_2$)$_p$—C(R$_4$)=CH$_2$, in which p denotes an integer between 1 and 10 and R$_4$ denotes a hydrogen atom or a C$_1$-C$_4$ straight or branched chain alkyl radical, with the proviso that one of the two radicals R$_1$ or R$_2$ denotes a residue—(CH$_2$)$_p$—C(R$_4$)=CH$_2$, R$_3$ denotes a hydrogen atom, a C$_1$-C$_8$ straight or branched chain alkyl radical or a C$_1$-C$_6$ straight or branched chain alkoxy radical, R$_5$ and R$_6$, which are identical or different, denote a C$_1$–C$_8$ straight or branched chain alkyl radical.

2. Compound according to claim 1, which is selected from the group consisting of diethyl 3-allyl-4-hydroxybenzalmalonate, diethyl 3-allyl-4-methoxybenzalmalonate, diethyl 3-metallyl-4-methoxybanzalmalonate, diethyl 4-allylbenzalmalonate, diethyl 4-methallylbenzalmalonate, diethyl 3-allyl-4,5-dimethoxybenzalmalonate, diethyl 3-allyl-4-butoxy-5-methoxybenzalmalonate and di-(2-ethylhexy) 3-allyl-4,5-dimethoxybenzalmalonate.

3. Cosmetic composition which comprises an effective quantity of at least one compound of formula (I) according to claim 1, in a cosmetically acceptable substrate containing at least one fatty phase.

4. cosmetic composition according to claim 3, which comprises, as compound (I), at least one of the compounds selected from group consisting of diethyl 3-allyl-4-hydroxybenzalmalonate, diethyl 3-methallyl-4-methoxybenzalmalonate, diethyl 3-methallyl-4-methoxybenzalmalonate, diethyl 4-allylbenzalmalonate, diethyl 4-methallylbenzalmalonate, diethyl 3-allyl-4,5-dimethoxybenzalmalonate, diethyl 3-allyl-4-butoxy-5-methoxybenzalmalonate and di-(2-ethylhexyl) 3-allyl-4,5-dimethoxybenzalmalonate.

5. Cosmetic composition according to claim 3, which is in the form of an oily or oleoalcoholic lotion, emulsion, oloealcoholic, alcoholic or hydroalcoholic gel, a solid stick or an aerosol.

6. Cosmetic composition according to claim 5, which additionally contains cosmetic adjuvants selected from the group consisting of thickeners, softeners, humectants, surfactants, preserving agents, antifoams, perfumes, oils, waxes, lanolin, lower monoalcohols and polyols, propellants, colorants and pigments.

7. Cosmectic composition according to claim 3, which forms a composition for protecting human skin and contains 0.25 to 3% by weight of compound of formula (I).

8. Cosmetic composition according to claim 3, which is in the form of a sunscreen composition and contains 0.5 to 15% by weight of compound of formula (I).

9. Cosmetic sunscreen composition according to claim 8, which additionally contains an agent filtering the UV-B or UV-A rays.

10. Cosmetic composition according to claim 3, intended to be applied to hair, which is in the form of a shampoo, lotion, gel or emulsion for rinsing, setting or treating lotion or gel, a lotion or gel for blow drying or setting, hair lacquer, a composition for permanent-waving, bleaching or dyeing and comprises 0.25 to 3% by weight of compound of formula (I).

11. Cosmetic composition according to claim 3, which is in the form of a coloured or uncoloured cosmetic composition, which consists of a hair-care composition, a makeup product or a composition for skin care or treatment, comprising 0.25 to 3% by weight of compound of formula (I).

12. Process for protecting skin and natural or sensitized hair against ultraviolet radiation, which consists in applying to the skin or hair an effective quantity of a cosmetic composition containing at least one unsaturated benzalmalonate derivative of formula (I) according to claim 1.

13. Process for protecting a cosmetic composition against ultraviolet rays, which consists incorporating in this composition an effective quantity of at least one compound of formula (I) according to claim 1.

14. A compound in accordance with claim 1 in which p is an integer between 1 and 4.

* * * * *